United States Patent [19]

Smith et al.

[11] Patent Number: 5,716,646
[45] Date of Patent: Feb. 10, 1998

[54] METHODS AND COMPOSITIONS FOR TREATING ARTHRITIS

[76] Inventors: Steven A. Smith; Lorraine J. Smith, both of 5706 S. 30th West Ave., Tulsa, Okla. 74107

[21] Appl. No.: 637,572

[22] Filed: Apr. 25, 1996

Related U.S. Application Data

[63] Continuation-in-part of Ser. No. 503,696, Jul. 18, 1995, which is a continuation-in-part of Ser. No. 985,610, Dec. 3, 1992, Pat. No. 5,433,954, which is a continuation-in-part of Ser. No. 518,170, May 1, 1990, Pat. No. 5,171,581.

[51] Int. Cl.$^6$ .......................... A61K 33/24; A61K 31/28
[52] U.S. Cl. .......................... 424/646; 424/617; 424/723; 514/501; 514/825
[58] Field of Search .......................... 424/646, 723, 424/617; 514/501, 825

[56] References Cited

U.S. PATENT DOCUMENTS

| | | | |
|---|---|---|---|
| 4,680,309 | 7/1987 | Maurer | 514/499 |
| 5,171,581 | 12/1992 | Smith et al. | 424/617 |
| 5,433,954 | 7/1995 | Smith et al. | 424/646 |

FOREIGN PATENT DOCUMENTS

| | | |
|---|---|---|
| 961502 | 1/1975 | Canada . |
| 025721 | 3/1981 | European Pat. Off. . |
| 77-08774 | 3/1977 | France . |
| 1-287033 | 11/1989 | Japan . |
| 9212952 | 8/1992 | WIPO . |
| 9412195 | 6/1994 | WIPO . |

OTHER PUBLICATIONS

WPIDS Abstract, accession No. 90-004033, 1990.
WPIDS Abstract, accession No. 81-23875D, 1981.
WPIDS Abstract, accession No. 79-00338B, 1979.
CAPLUS Abstract, accession No. 1975:139781, 1975.
WPIDS Abstract, accession No. 87-288460, 1987.
Brauner, Gary J., M.D., "Seborrheic Dermatitis" (found in Section 17, Miscellaneous disorders arising in the skin, *Dermatology in General Medicine*, (Textbook and Atlas, McGraw–Hill Book Company), Second Edition, pp. 803–807 (1979).
DaCosta, J.M., M.D., "Observations on the salts of nickel, especially the bromide of nickel", *The Medical News, A Weekly Journal of Medical Science*, vol. XLIII, No. 13, pp. 337–338, (Sep. 29, 1983).
Domonkos, Anthony N., F.A.C.P., et al., "Seborrheic Dermatitis, Psoriasis, Recalcitrant Pustular, Eruptions and Erythorderma", *Andrews' Diseases of the Skin*, (Textbook, W.B. Saunders Company), Seventh Edition, p. 218 (1982).

Even–Paz, Zvi, M.D., et al., "The Dead Sea and Psoriasis—Historical and Geographic Background", *International Journal of Dermatologym* vol. 28, No. 1, pp. 1–7 (Feb. 1989).
Gawkrodger, D.J., et al., "Nickel dermatitis: the reaction to oral nickel challenge", *British Journal of Dermatology*, vol. 115, pp. 33–38 (1986).
Hurwitz, S., M.D., "Eczematous Eruptions in Childhood", *Clinical Pediatric Dermatology* (Textbook, W.B. Saunders Company), p. 39, (1981).
Jordan, William P., Jr. M.D., et al., "Nickel feeding in nickel–sensitive patients with hand eczema", *Journal of the American Academy of Dermatology*, pp. 506–508 (Dec. 1979).
Kolipinski, L., M.D., "On the Uses of Nickel Sulphate in Medicine", Cyclopaedia & Medical Bulletin, pp. 348–355, (1911).
List, P.H., et al., "Niccolum", *Hagers Handbuch der Pharmazeutischen Praxis*, p. 189, Springer–Verlag (1977).
Miller, Mary Jo, M.S., et al., "Nickel", prepared by Bureau of Toxic Substance Assessment, New York State Dept. of Health, Abstract and pp. 5 and 5, Aug. 1989.
Moschella, Samuel L., M.D., et al., "Dermatitis", *Dermatology*, (Textbook, W.B. Saunders Company) vol. 1, Second Edition, pp. 356–361 (1985).
Ormsby, Oliver S., M.D., et al., "Superficial Mycoses Including Dermatomycoses", *Diseases of The Skin*, (Textbook, The C.V. Mosby Company) p. 1097, (1948).
Sutton, Richard L., et al., "Disease Due to Higher Fungi" *Diseases of The Skin*, (Textbook, The C.V. Mosby Company) p. 1044, (1939).
Soter, Nicholas A., M.D., et al., "Cutaneous changes in disorders of altered reactivy: eczematous dermatitis, Introduction and classification", *Dermatology in General Medicine*, (Textbook and Atlas, McGraw–Hill Book Company), Second Edition, pp. 507–509 (1979).
*The Merck Index*, #6340. Nickel Bromide, p. 932 (1983).
"Seborrheic Dermatitis", American Academy of Dermatology (leaflet) (1984).

*Primary Examiner*—John Pak
*Attorney, Agent, or Firm*—Steinberg, Raskin & Davidson, P.C.

[57] ABSTRACT

Arthritic conditions treated by oral administration of inorganic nickel compound(s), with or without bromide(s). In an especially preferred embodiment, the nickel compound used to treat these conditions is $NiBr_2$.

7 Claims, No Drawings

METHODS AND COMPOSITIONS FOR TREATING ARTHRITIS

This application is a continuation-in-part of U.S. Ser. No. 08/503,696 filed Jul. 18, 1995, which is a continuation-in-part of U.S. application Ser. No. 07/985,610 filed Dec. 3, 1992, now U.S. Pat. No. 5,433,954, which is a continuation-in-part of U.S. application Ser. No. 07/518,170 filed May 1, 1990, now U.S. Pat. No. 5,171,581.

BACKGROUND OF THE INVENTION

The skeletal system of mammals is a complex interactive network which provides a rigid framework which protects internal organs and facilitates motion. To assist motion, joints allow movement of one bone upon another. The ends of the bones are covered with hyaline cartilage, and diarthrodial joints are covered by collagenous tissue called the joint capsule. The synovial membrane lines the space side of the joint capsule. The synovial membrane is a relatively acellular, highly vascular, delicate membrane which secretes the synovial fluid. Cartilage is vascular and derives its nutrition from the synovial fluid located within the joint capsule.

Various inflammatory diseases, trauma and degeneration may afflict the joint. Arthritis is a group of diseases and\or conditions which adversely affect skeletal system, in general, particularly the joints. Each type of arthritis is characterized by its own distinctive manifestations and presentations. Rheumatoid arthritis (RA) is a chronic systemic illness manifested primarily by inflammatory arthritis which usually involves symmetrical affliction of small peripheral joints. The disease may also affect the cardiovascular, hematologic and pulmonary systems, and the ocular system. Rheumatoid arthritis is distinguished from other types of arthritis by the presence of a rheumatoid factor in the blood serum.

Degenerative joint diseases (DJD), also known as osteoarthritis and hypertrophic arthritis, are characterized by loss of joint cartilage and hypertrophy of bone. Stress and wear are thought to contribute to the loss of cartilage in certain patients.

Arthritis may be induced by deposition of crystals such as sodium urate, calcium pyrophosphate dehydrate and hydroxyapatite within the joint capsule.

Psoriatic arthritis is yet another type of arthritic condition, but is less well understood than the aforementioned arthritic conditions. It causes pain, swelling and tenderness of the joints and the tissue around the joints. Statistically, about ten percent of people with psoriasis develop psoriatic arthritis. There are certain genetic markers in patients with a family history of the disease, suggesting that this condition may have a genetic component. Psoriatic arthritis may also develop after a joint injury. Psoriatic arthritis has been linked with rheumatoid arthritis, but can be differentiated in several ways. First, the blood serum of patients with this condition lacks the rheumatoid factor which is present in patients with rheumatoid arthritis. Second, unlike rheumatoid arthritis, the psoriatic arthritis may effect the distal joints of the fingers and toes. Third, the presence of nail realformation and psoriasis are indicative of psoriatic arthritis, but are not generally present in patients with rheumatoid arthritis. It has been demonstrated that when certain immune cells are depleted in HIV-infected patients, those patients with rheumatoid arthritis improve while those with psoriatic arthritis do not.

For years there have been many attempts to treat the various types of arthritis, and several topical and systemic treatments for arthritis have been with varying degrees of success. Numerous systemic drugs are employed in the treatment of arthritis including non-steroidal antinflammatories, corticosteroids, opioid and non-opioid analgesics, anti-malarials, gold, and cytotoxic agents such as methotrexate. Topical preparations such as those including capsacian, salycilate analgesics, corticosteroids, and counterirritants are also employed. Numerous adverse reactions have been reported with traditional pharmacotherapy, particularly with systemic treatment.

Despite the foregoing advances, there is a need in the art for new treatments for arthritis which do not exhibit the toxicity and/or side effects associated with traditional arthritis therapies.

SUMMARY OF THE INVENTION

The present invention is directed to methods and compositions for the systemic treatment of arthritis.

Specifically, the present invention is directed to pharmaceutical formulations including pharmaceutically acceptable nickel compound(s). Preferably, the pharmaceutical formulations also include an accompanying bromide compound(s). The inventive compositions are administered to diseased subjects over time with alleviation of the signs and symptoms of the disease(s). The formulations may be administered either alone or in combination with other anti-arthritic treatments known in the art.

More particularly, the present invention is related to a method of treating human beings for arthritis comprising the steps of orally administering an effective mount of a disease-inhibiting formulation containing a non-toxic, pharmaceutically acceptable nickel (Ni) compound(s) in a human patient, and dosing the patient such that the formulation provides an amount of nickel from about 1 to about 300 mcg/kg (micrograms per kilogram) of patient weight/day. Preferably the patient is administered a unit dose of the formulation containing about 0.02 to about 10 mg nickel at least once every other day. The unit dose is preferably administered to a patient on a once daily basis. In a preferred embodiment, the nickel compound is $NiBr_2$, $NiSO_4$, $NiCl_2$, mixtures of any of the foregoing, etc. In an especially preferred embodiment, the nickel compound is nickel bromide ($NiBr_2$).

For purposes of this application, the term "nickel" includes elemental nickel and nickel ions and nickel compounds; the term "bromide" includes elemental bromide formulation, bromide ions, and bromide compounds.

The present invention is also related to pharmaceutical formulations for treating arthritis in patients comprising from about 0.02 to about 10 mg Ni/ml. A unit dose of a pharmaceutical formulation prepared in accordance with this invention preferably includes nickel (Ni) in an amount from about 1 to about 300 mcg/kg (micrograms per kilogram) of patient weight/day. Preferably, the nickel is provided by a non-toxic pharmaceutically acceptable Ni compound(s). The formulation may be in any pharmaceutically acceptable form for systemic administration, including liquid, capsule, and tablet form. In a preferred embodiment, the formulation is a liquid and nickel is present in an amount of from about 0.15 to about 4.5 mg Ni ml. In most preferred embodiments, the formulations include an effective amount of bromide to render an anti-arthritic effect in the patient.

When bromide is present in the formulation, the ratio of bromide:nickel preferably is about 2.5:1 to about 50:1 and more preferably from about 5:1 to about 20:1.

DETAILED DESCRIPTION

The exact etiologies of the arthritic diseases are not known, and mechanism of action of this invention is not known. However, the use of nickel or nickel/bromide compositions to treat psoriasis, seborrheic dermatitis and eczema was previously reported in U.S. Pat. Nos. 5,171,581 and 5,433,954, hereby incorporated by reference in their entireties.

One aspect of the present invention is directed to pharmaceutical formulations comprising an effective amount of a non-toxic pharmaceutically acceptable nickel compound. Preferably, the pharmaceutical formulations include nickel in an amount of from about 0.02 to about 6 mg Ni/ml. Preferably, the pharmaceutical formulations comprise from about 0.15 to about 4.5 mg Ni/ml, and most preferably from about 0.19 to about 4.1 mg Ni/ml.

Another aspect of the present invention is directed to a unit dose of an oral pharmaceutical formulation for treating arthritis in human patients comprising from about 1 to about 300 mcg/kg patient weight, the dosage of nickel being derived from a non-toxic pharmaceutically acceptable nickel compound, such as those described herein. Preferably the unit dose further includes a bromide compound such that the amount of bromide in the pharmaceutical formulation is in a ratio of bromide:nickel ranging from about 2.5:1 to about 50:1.

The nickel compound is preferably a non-toxic, pharmaceutically acceptable nickel compound(s). The nickel compounds that may be incorporated into the pharmaceutical formulations include any pharmaceutically acceptable organic or inorganic nickel compounds. Preferred inorganic nickel compounds include nickel sulfate, nickel dibromide, and combinations thereof. Nickel dibromide is most preferred.

Preferably, the pharmaceutical formulations include bromide in an amount of from 1 to about 100 mg Br/ml. More preferably, bromide is present in the pharmaceutical formulation in an amount of from about 5.5 to about 90 mg Br/ml.

The role of bromide is not fully understood at this time, but it appears to be one of facilitator, either through physiological assistance in nickel transport, or some more direct action. Bromide, however, is not an absolute requirement for utility of this invention.

The bromide may be provided by any non-toxic pharmaceutically acceptable organic or inorganic bromide compound. Preferred inorganic bromide compounds include sodium bromide, nickel dibromide, potassium bromide, ammonium bromide, and mixtures thereof. Potassium bromide is preferred.

The formulations of the present invention preferably include from about 1–99.99% pharmaceutically acceptable vehicle, such as water, polyethylene glycol solutions, saccharide solutions, and the like.

Pharmaceutical adjuvants are preferably included in the formulations of the present invention in amounts of from 0.01 to 99.99% of the final formulation, w/v or w/w. Suitable pharmaceutical adjuvants include pharmaceutical excipients known in the art such as stabilizers, viscosity agents, sucrose, flavorants, colorants and the like. Presence of these adjuvants is not critical to the composition.

The formulations of the present invention may also include a pharmaceutically acceptable amount of preservative(s). Suitable preservatives include ionizable salts, organic compounds, and mixtures thereof. When the preservative is an ionizable salt, sodium chloride and potassium chloride are preferred. Ionizable salts used as stabilizers will be present in amounts of from about 0.005 to about 100 mcg/ml of the final formulation. When the preservative is an organic compound, e.g., ethanol, it is present in amounts of from 5 to about 50% by volume of the final formulation.

In addition to the above, the formulations of the present invention may also include homeopathics known in the art to be useful for the treatment of arthritis. A non-limiting list of suitable homeopathics include cimicifuga racemosa, rhus toxicodendron, bryonia, and combinations thereof.

In an especially prefered embodiment, the formulation is a 300 mg tablet with a lactose base containing 1.0 mg nickel ions from nickel sulfate and 10 mg bromide ions from potassium bromide and sodium bromide.

The formulations of the present invention may be prepared according to any means known in the art. Preferably, the dosage form is prepared by incorporating the requisite amount of nickel compound with the vehicle. The requisite amount of bromide compound may also be added, as well as any other pharmaceutical adjuvants or homeopathic compositions.

The formulations of the present invention are preferably solutions, although the final dosage form may also be in the form of a capsule or tablet.

Another aspect of the invention is directed to a method of treating arthritis in human patients, comprising orally administering a pharmaceutical formulation comprising from about 1 to about 300 mcg/kg patient weight of nickel per day for a period of time to substantially alleviate or improve the symptoms of the arthritis, wherein said nickel is derived from a non-toxic, pharmaceutically acceptable nickel compound. Preferably, the nickel compound, e.g., $NiSO_4$ is orally administered to the patient in doses within the range of about 0.2 mg Ni every other day to about 6 mg per day. Preferably, the dose of nickel administered is from about 0.4 to about 3.7 mg Ni/day, and most preferably 0.4 to 3.0 mg Ni/day. Preferably the nickel is derived from $NiBr_2$.

When bromide is also administered to treat arthritic conditions, bromide is administered in an amount sufficient to render an anti-arthritic effect. Preferably, the bromide (Br) is administered in doses ranging from 1ing Br every other day to about 100 mg Br/day. The bromide can be administered simultaneously with or separate from the nickel dose. Preferably, the bromide is administered such that the ratio of bromide to nickel is in the range of from about 2.5:1 to about 50:1.

In preferred embodiments, an arthritic patient, e.g a human patient, is treated by administration of from about 0.1 to about 40 ml. of the pharmaceutical compositions prepared according to the present invention. Most preferably, the formulation is administered orally.

In preferred embodiments, the formulations are administered to a patient in combination with or as an adjunct to conventional arthritis treatments known in the art, e.g. non-steroidal antiinflammatories, topical preparations, corticosteroids, analgesics, etc. The amount of the formulation administered is sufficient to render an anti-arthritic effect. The anti-arthritic effect can be determined, e.g. by subjective or objective criteria such as decreased pain, increased joint mobility or other criteria known in the art to document improvements in arthritic conditions.

DETAILED DESCRIPTION OF PREFERRED EMBODIMENTS

The following examples illustrate various aspects of the present invention. They are not to be construed to limit the claims in any manner whatsoever.

Case Studies in Treating Arthritis with Nickel and Bromide Compounds

Clinical case studies were performed on subjects selected from the patient base at the clinic of Dr. Steven A. Smith.

Subjects were selected by Dr. Smith on the basis of a history of chronic arthritis. Study medication was prescribed for the subjects as an addition to their pre-existing treatment regimen. Evaluation criteria used were: frequency and severity of arthritic pain; joint flexibility and ease of motion; stability of the disease condition; reduction or increase in types, strengths or amounts of concurrent medications required to control the arthritis. These evaluations were dependent on questioning subjects or those frequently with the subject or caring for the subject about their observations and experience with the disease condition.

Standard treatment charts were maintained on each subject, with a history of the patient's arthritis and its treatment pattern being taken to establish a baseline. Subjects were typically seen for evaluation and adjustment of their medications monthly. Some subjects were also being treated concurrently for other conditions in addition to arthritis.

Five difference formulations of the study medications were used in evaluating the use of the minerals nickels and bromide in low dosages to treat arthritis. The bromide is delivered in the form of potassium bromide and/or sodium bromide and the nickel in the form of nickel sulfate; all in an aqueous solution. The nickel and bromide content shown were assayed by the University of Virginia Health Sciences Center Trace Minerals laboratory:

(1) Formula D consisted of bromide ions at a concentration of 5.01 mg/ml from Sodium bromide and Potassium bromide, and nickel ions at a concentration of 0.23 mg/ml from Nickel sulfate; the aqueous solution also contained sodium chloride (0.065 mcg/ml) and 20% alcohol as a preservative.

(2) Formula A consisted of bromide ions as a concentration of 5.75 mg/ml from Potassium bromide and nickel ions at a concentration of 0.25 mg/ml from Nickel sulfate; the solution also contained other homeopathic attenuations of natural substances indicated in literature for symptoms of Arthritis and Rheumatism: dilute amounts of cimicifuga racemosa, rhus toxicodendron, and bryonia, along with 12% alcohol as a preservative.

(3) Formula S consisted of bromide ions at a concentration of 5.2 mg/ml from Sodium bromide and Potassium bromide, and nickel ions at a concentration of 0.19 mg/ml from Nickel sulfate; the aqueous solution also contained sodium chloride (0.065 mcg/ml) and 20% alcohol as a preservative.

(4) Formula G consisted of bromide ions at a concentration of 82 mg/ml from Sodium bromide and nickel ions at a concentration of 4.1 mg/ml from Nickel sulfate; the aqueous solution contained only distilled water.

(5) Formula P consisted of bromide ions at a concentration of 6.5 mg/ml from Sodium bromide, Potassium bromide, and Zinc bromide and nickel ions at a concentration of 0.6 mg/ml from Nickel sulfate; the aqueous solution also contained Potassium sulfate and 9% alcohol as a preservative.

(6) Formula T consists of 300 mg tablets with a lactose base containing 1.0 mg nickel ions from nickel sulfate and 10 mg bromide ions from potassium bromide and sodium bromide.

Ten subjects were recruited for the study stating in July of 1994. No adverse events or side effects were reported by the subjects during the study and none dropped out. Eight subjects exhibited distinct improvement while taking their study medication as compared to their previous condition or disease pattern:

Case No. 1

This patient is a 36 year old Hispanic male with a history of psoriatic plaques and joint pain. Dr. Smith first saw the patient in June of 1994 in order to the treat the plaques on his scalp, legs, elbows, and nails and psoriatic joint pain in his left elbow, both hands, and left ankle and foot. In addition, the patient was loosing sleep due to the pain of psoriatic arthritis. On September, 1994, the patient reported that he was taking acetaminophen, as well as ketoprofen (50 mg/day) for the arthritis although he still had painful, tender, swollen joints, especially in his hands. On Oct. 3, 1994, he reported that his psoriasis and arthritis was worsening. The patient was put on a treatment regiment of methotrexate 10 mg/week for the psoriasis and psoriatic arthritis and topical Ternovate™ ointment and Temovate™ Gel for the psoriasis. Approximately 30 days after staring this treatment, the patient reported increased pain in his hands, feet, and hips. Ibuprofen 400 mg four times daily as needed was added to the treatment regimen. By Jan. 17, 1995 the patient reported terrible joint pain and worsening psoriasis. At this time, 4 ml daily of Formula P was added to this treatment. One month later, the patient reported an improvement in both the psoriasis and psoriatic arthritis and stated that he no longer need to take the ibuprofen for pain. Formula P was increased to 6 ml daily. During a follow-up on May 24, 1995, the patient reported worsening psoriasis and psoriatic arthritis. The treatment regimen was continued and the patient reported an improvement in psoriatic arthritis on Aug. 15, 1995. By Sep. 25, 1995, the patient reported that the joint pain was almost gone and stated that there was a general improvement in overall health.

Case No. 2

This patient is a 67 year old female who was referred to Dr. Smith on Oct. 15, 1994 for treatment of extensive pruritic red skin on her arms and hand, including palms On May 17, 1995, the patient complained of aches and pains and general malaise and arthritis symptoms. At this time, the patient was entered into the study and given 7 ml of Formula A daily. After 3 weeks, the patient reported that the arthritis pain in her shoulders was much improved. The dose of Formula A was reduced to 5 ml and the patient continued for 2 more months. During a follow-up conversation on Sep. 19, 1995, the patient stated that Formula A was more effective than other treatments that she had used to treat her gout and arthritic joints (knuckles and shoulder).

Case No. 3

This patient is a 38 year old female weighing 160 lbs (73 kg) with a 9 year history of psoriasis and psoriatic arthritis. Prior to starting this study, the patient was treated with UVB treatments and attained 75% improvement in her psoriatic condition. Further treatments included a combination of UVA and UVB treatments, Dovonex™ ointment, and Oruvail™ or ibuprofen. The patient's psoriatic arthritis only improved a little. The patient was entered into the study on January of 1995 and started on 7 ml of Formula P. After only 3 months of using Formula P, the patient reported that her psoriatic arthritis had really improved and swelling in her hands and feet had decreased by half and were continuing to decrease. At this time, she required additional pain relievers only intermittently. Her dose of Formula P was decreased to 5 ml and one month later (May 23, 1995), her psoriatic arthritis continued to improve. In addition, her requirement for additional pain relievers (Advil™) was reduced from 5 to 2 or 3 pills a day. At this time, her medication was changed to 0.14 ml Formula G. On Jun. 13, 1995, the patient reported no arthritis pain. She had reduced the dose of Formula G to 0.12 ml every other day and was not taking any more Advil™. In addition, her psoriasis had improved and was stable. The patient continued taking 0.12 ml Formula G every other day. On Oct. 10, 1995, the patient's psoriasis and psoriatic arthritis was still stable. At this time she was changed to one tablet of Formula T every other day, to be gradually reduced to ¼ tablet every other day for maintenance control. On Feb. 6, 1996 she was examined; her psoriasis was mild and under control. She reported that no arthritic symptoms were evident.

Case No. 4

This patient is a 88 year old female who first saw Dr. Smith in 1990 for psoriasis. She had been treated previously with Diprolene™ ointment, tar, and UVB with some success. On Dec. 7, 1994, the patient was admitted to the study and started on 4 ml daily of Formula S. On Jan. 18, 1995, the formula was changed to Formula P. By Sep. 7, 1995, the patient reported that her arthritis had much improved since taking the nickel therapy.

Case No. 5

This patient is a 75 year old, 236 lb, caucasian female who first presented to Dr. Smith on Jan. 13, 1995 for scaling on her scalp, arms, legs, and elbows. Her current medications included Dyazide™, Synthroid™, Proventil™, Vanceril™, Novahistine™ (as needed), Daypro™ (as needed for arthritis), and Atrovent™. She was entered into the study at this time and started on Formula P, 8 ml daily. She was also instructed to use Dovonex™ ointment and Nizoral™ shampoo. On Feb. 10, 1995, she reported an improvement in the psoriasis and arthritis symptoms. Formula P was increased to 10 ml daily. On May 9, 1995, the patient's treatment was changed to 0.4 ml of Formula G and then reduced to 0.3 ml of Formula G on May 23, 1995. By Jun. 8, 1995, the psoriasis on her scalp and body had improved and her joints were better and more mobile.

Case No. 6

This patient is a 47 year old, 190 lb, caucasian male with a history of severe psoriasis and psoriatic arthritis in his ankles, back, and other large joints. The patient had previously undergone many types of treatments for both the psoriasis and psoriatic arthritis with very little success. The patient was entered into the study on Jul. 29, 1994 with moderate arthritis pain, swelling, and stiffness. He was started on Formula G, 0.4 ml daily. On Aug. 12, 1994, the dosage of Formula G was increased to 0.7 ml daily. Since then, he has taken Formula S (0.7 ml daily) and Formula P (0.7 ml daily), and his psoriatic arthritis has improved in his feet, back, and ankles (including marked improvement in his Achilles tendinitis).

Case No. 7

This patient is a 49 year old Caucasian female was first seen by Dr. Smith Mar. 16, 1994 for psoriasis (10 year history) over her entire body and arthritis in most joints. The patient was entered into the study on Aug. 24, 1994 and started on 0.3 ml Formula G daily. After one month, her arthritic condition worsened moderately and the dose of Formula G was doubled to 0.6 ml. One Feb. 27, 1995, the patient had severe pain, swelling, and stiffness in her right hand. At this time, the patient was taken off Formula G and given Formula P, 8 ml daily. On May 17, 1995, the patient reported that her joint pain may have improved since beginning the study.

Case No. 8

This patient is a 41 year old, 180 lb. caucasian female with a 21 year history of arthritis and psoriasis. First seen by Dr. Smith on Mar. 10, 1994, the patient had red, thin psoriasis plaques on her arms and legs and several painful arthritic joints (ankles, toes, knees, back, hip, wrist, fingers, and neck). At that time, the only effective therapy for the psoriasis was UV light treatments. She also took 800 mg ibuprofen one to two times daily for her arthritis symptoms. The patient was admitted to the study on Jul. 18, 1994 and was started on 0.4 ml of Formula G to study its effects on both psoriasis and arthritis.

After 4 weeks on the study medication she had improved only slightly, so her dose was doubled to 0.8 ml/day. At the next four week evaluation, the patient reported that since the dose had been doubled (four weeks earlier), she had noticed marked improvement in both her psoriatic condition and arthritic joints. She stated that the arthritis was better than it had been in 20 years. Subsequent follow-ups at four week intervals reported only mild arthritic symptoms of stiffness in joints and no pain or swelling. The patient continued taking 600–800 mg ibuprofen once a day for these mild symptoms. The dose level was dropped back to 0.4 ml/day after 16 weeks and the patient discontinued the Formula G after 20 weeks. At 24 weeks (2 weeks off study medication), moderate joint pain had returned in her toes and back. On Jan. 5, 1995, the patient was started on 15 ml Formula S. She discontinued on Feb. 8, 1995 in a state of near-remission from her arthritis. On Apr. 3, 1995, the patient reported a return of pain associated with psoriatic spondylitis.

Case No. 9

This patient is an approximate 200 lb, 69 year old Caucasian male with a history of chronic seborrheic dermatitis. The patient was first seen by Dr. Smith on Jun. 5, 1995. The patient exhibited the symptoms of seborrheic dermatitis and, in addition, reported a moderate degree of pain and discomfort in his joints, particularly his knees. The patient was started on a dose of 10 ml per day of Formula D to study its effects on both seborrheic dermatitis and arthritis. The arthritis was diagnosed as a form of rheumatoid arthritis.

The patient's arthritis symptoms were again evaluated on Sep. 19, 1995. He reported that his knee pain was considerably better while on study medication than had been his "normal" historical experience. He also reported, however, that he was still taking Naprosyn™ for neck pain.

Case No. 10

This patient is a 64 year old Caucasian male, approximately 175 lbs, who was first seen by Dr. Smith on Jun. 24, 1988 for psoriasis and psoriatic arthritis. At that time, he was using several medications and undergoing PUVA therapy with no response. This continued, with only minor improvements, for several years. On Jan. 30, 1995, the patient was entered into the study. In addition to his current medications (Pravachol™ 20 mg, meclizine 25 mg, Theolair™ 250 mg), the patient was started on 7 ml daily of Formula P, erythromycin ointment 3.5 gm, Derma Smooth™, and Tegrin™ Shampoo. A mild improvement was seen in his psoriatic condition on Mar. 30, 1995 and the dose for Formula P was increased to 8 ml daily. The patient discontinued the Formula P in July 1995, at which time he had no complaints about the psoriatic arthritis.

The examples provided above are not meant to be exclusive. Many other variations of the present invention would be obvious to those skilled in the art, and are contemplated to be within the scope of the appended claims.

What is claimed is:

1. A method of treating arthritis in a human patient comprising administering from about 0.1 to about 5 mg nickel/day and from about 1 to about 100 mg bromide/day to said patient.

2. The method of claim 1, further comprising administering to said patient an active agent selected from the group consisting of a topical corticosteroid, a systemic corticosteroid, an antibiotic and combinations thereof.

3. A method of treating arthritis in a human patient comprising simultaneously administering from about 0.1 to about 5 mg nickel/day and from about 1 to about 100 mg bromide/day to a patient in need thereof.

4. A method of treating psoriatic arthritis in a human patient comprising simultaneously administering from about 0.1 to about 5 mg nickel/day and from about 1 to about 100 mg bromide/day to a patient in need thereof.

5. A method improving the pharmacotherapy of a human patient undergoing pharmacotherapy for arthritis, comprising co-administering from about 0.1 to about 40 mls of a pharmaceutical formulation comprising about 0.02 to about 10 mg nickel and bromide, where the weight ratio of said bromide to said nickel in said formulation is from about 2.5:1 to 50:1, to said patient at least every other day in addition to the patient's pharmacotherapy for arthritis.

6. A method of treating arthritis in human patients, comprising orally administering a unit dose of a pharmaceutical formulation comprising from about 1 to about 300 mcg/kg patient weight of nickel and bromide, where the weight ratio of said bromide to said nickel in said formulation is from about 2.5:1 to 50:1, per day for a period of time to substantially alleviate or improve the symptoms of the arthritis, said nickel being derived from a non-toxic, pharmaceutically acceptable nickel compound.

7. The method of claim 6, wherein said nickel compound is $NiBr_2$.

* * * * *